United States Patent
Yonehara et al.

(10) Patent No.: US 7,354,732 B2
(45) Date of Patent: Apr. 8, 2008

(54) METHOD OF ASSAY WITH SULFONIC ACID COMPOUND AND NITRO COMPOUND

(75) Inventors: Satoshi Yonehara, Kyoto (JP); Kaori Ishimaru, Kyoto (JP); Kaoru Hirai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 10/517,853

(22) PCT Filed: Apr. 28, 2003

(86) PCT No.: PCT/JP03/05486

§ 371 (c)(1),
(2), (4) Date: Dec. 14, 2004

(87) PCT Pub. No.: WO03/107011

PCT Pub. Date: Dec. 24, 2003

(65) Prior Publication Data

US 2005/0221415 A1    Oct. 6, 2005

(30) Foreign Application Priority Data

Jun. 14, 2002    (JP) ............................. 2002-174896

(51) Int. Cl.
*C12Q 1/26*    (2006.01)
*C12Q 1/28*    (2006.01)

(52) U.S. Cl. .......................... 435/25; 435/28

(58) Field of Classification Search .................... None
See application file for complete search history.

(56) References Cited

U.S. PATENT DOCUMENTS

| | | | |
|---|---|---|---|
| 4,119,405 A | 10/1978 | Lam | |
| 4,310,626 A | 1/1982 | Burkhardt et al. | |
| 4,587,220 A | 5/1986 | Mayambala-Mwanika et al. | |
| 4,743,559 A | 5/1988 | Koevér et al. | |
| 4,755,472 A | 7/1988 | Ismail et al. | |
| 4,954,451 A | 9/1990 | Albarella et al. | |
| 5,677,272 A | 10/1997 | Ghosh et al. | |
| 5,810,944 A | 9/1998 | Smitkowski et al. | |
| 5,902,731 A * | 5/1999 | Ouyang et al. | 435/26 |
| 6,127,138 A | 10/2000 | Ishimaru et al. | |
| 6,200,773 B1 | 3/2001 | Ouyang et al. | |
| 6,790,665 B2 | 9/2004 | Yonehara et al. | |
| 2002/0025546 A1* | 2/2002 | Komori et al. | 435/28 |
| 2002/0173043 A1* | 11/2002 | Merabet et al. | 436/66 |
| 2003/0162242 A1 | 8/2003 | Yonehara | |
| 2004/0063213 A1 | 4/2004 | Hirai et al. | |

FOREIGN PATENT DOCUMENTS

| | | |
|---|---|---|
| EP | 1 002 874 | 5/2000 |
| JP | 56-151358 | 11/1981 |
| JP | 57-13357 | 1/1982 |
| JP | 57-161650 | 10/1982 |
| JP | 59-193354 | 11/1984 |
| JP | 60-168050 | 8/1985 |
| JP | 61-000084 A | 1/1986 |
| JP | 62-169053 | 7/1987 |
| JP | 2-69644 | 3/1990 |
| JP | 3-30697 | 2/1991 |
| JP | 9-185021 | 7/1997 |
| JP | 11-196897 | 7/1999 |
| JP | 10-210967 | 8/1999 |
| JP | P2001-292795 A | 10/2001 |
| WO | 02/06519 | 1/2002 |
| WO | 02/27331 | 4/2002 |

OTHER PUBLICATIONS

Oshiro et al. New Method for Hemoglobin Determination by Using Sodium Lauryl Sulfate (SLS); Clinical Biochemistry, vol. 15, Issue 1 (1982). pp. 83-88.*

U.S. Department of Health and Human services, Agency for Toxic Substances and Disease Registry (ATSDR) Case Studies in Environmental Medicine: Nitrate/Nitrite Toxicity, Course: SS3054 (2001)☐☐www.atsdr.cdc.gov/HEC/CSEM/.*

Methemoglobinemia: Primary Industrial Chemicals and Non-Occupational Exposures; http://www.haz-map.com/methem.html.*

U.S. Department of Health and Human services, Agency for Toxic Substances and Disease Registry (ATSDR) Case Studies in Environmental Medicine: Nitrate/Nitrite Toxicity, Course: SS3054 (2001)http://www.atsdr.cdc.gov/HEC/CSEM/.*

Goodwin, et al., "Quantification of Protein Solutions with Trinitrobenzenesulfonic Acid", Clinical Chemistry, vol. 16, No. 1, 1970.

Oshiro, et al., "New Method for Hemoglobin Determination by Using Sodium Lauryl Sulfate (SLS)", Clin. Biochem., vol. 15, No. 1, p. 83-88.

Johnson, et al., "Oxidant Damage to Erythrocyte Membrane in Glucose-6-Phosphate Dehydrogenase Deficiency: Correlation with in Vivo Reduced Glutathione Concentration and Membrane Protein Oxidation", Bloc, vol. 83, No. 4, pp. 1117-1123.

(Continued)

*Primary Examiner*—Jon Weber
*Assistant Examiner*—Paul Martin
(74) *Attorney, Agent, or Firm*—Hamre, Schumann, Mueller & Larson, P.C.

(57) ABSTRACT

A method for measuring an analyte in a sample by using a redox reaction is provided, which gives values with excellent reliability. Prior to the redox reaction, at least one of a sulfonic acid compound and a nitro compound is added to the sample to eliminate the influence of hemoglobin and any hemoglobin degradation products as reducing substances contained in the sample. Subsequently, a reducing or oxidizing substance derived from the analyte is caused to generate, and the amount thereof is measured by the redox reaction. The amount of the analyte is determined from the measurement value. The sulfonic acid compound may be sodium lauryl sulfate, and the nitro compound may be 4-nitrophenol, etc.

17 Claims, No Drawings

OTHER PUBLICATIONS

Oshiro, et al., "New Method for Hemoglobin Determination by Using Sodium Lauryl Sulfate (SLS)", Clin. Biochem., vol. 15, No. 1, p. 83-88 (1982).

Johnson, et al., "Oxidant Damage to Erythrocyte Membrane in Glucose-6-Phosphate Dehydrogenase Deficiency Correlation with in Vivo Reduced Glutathione Concentration and Membrane Protein Oxidation", Bloc, vol. 83, No. 4, p. 1117-1123 (1994).

Gajjar, et al., "Activation and Stabilization of Enzymes Entrapped into reversed Micelles: Studies on Hydrolyzing Enzymes—Protease and $\alpha$-Amylase", Applied Biochemistry and Biotechnology, vol. 49, 1994, pp. 101-112.

Sidelmann, et al., "The effect of chemical anti-inhibitors on fibrinolytic enzymes and ihibitors", Clinica Chimica Acta 261, 1997 43-56.

* cited by examiner

METHOD OF ASSAY WITH SULFONIC ACID COMPOUND AND NITRO COMPOUND

TECHNICAL FIELD

The present invention relates to a method for measuring an analyte in a sample by using a redox reaction.

BACKGROUND ART

Conventionally, the measurement of the amount of an analyte in a sample using a redox reaction has been utilized for a wide range of applications. For example, such measurement has been utilized for measuring glycated proteins in applications such as biochemical analyses, clinical tests, and the like.

For instance, glycated proteins in blood, particularly glycated hemoglobin in erythrocytes, are significant indicators in the diagnosis, therapy and the like of diabetes because they reflect the patient's past history of blood glucose levels. Such glycated proteins in erythrocytes are measured using the above-noted redox reaction, for example, in the following manner.

First, erythrocytes are hemolyzed to prepare a sample. This hemolyzed sample is treated with a fructosyl amino acid oxidase (hereinafter, referred to as "FAOD") so that the FAOD is allowed to act on a glycated portion of the glycated protein, thus generating hydrogen peroxide. The amount of this hydrogen peroxide formed corresponds to the amount of the glycated protein. Then, a peroxidase (hereinafter, referred to as "POD") and a substrate that develops color by oxidation (a chromogenic substrate) further are added to this sample, so that a redox reaction occurs between the hydrogen peroxide and the chromogenic substrate with the POD as a catalyst. At this time, since the oxidizing substrate develops color when it is oxidized, the amount of the hydrogen peroxide can be determined by measuring the color developed. As a result, the amount of the glycated protein in erythrocytes can be determined.

However, various kinds of reducing substances such as ascorbic acid (AsA) and bilirubin usually are present in blood. Moreover, various kinds of reducing substances such as glutathione (GSH) are present in erythrocytes. These reducing substances may, for example, reduce the hydrogen peroxide, may inhibit the redox reaction, or may reduce the reducing agent after it develops color, which causes degradation of the color. Therefore, there has been a problem that it is difficult to determine the amount of the glycated protein in erythrocytes accurately.

Also, there has been another problem that the accuracy of the determination may deteriorate because the concentration of the contained reducing substances is not constant in each sample.

In order to avoid these problems, for example, various kinds of oxidizing agents have been added to samples. For example, JP 56(1981)-151358 A discloses a method of using halogen oxides such as iodic acid or periodic acid as oxidizing agents. JP 57(1982)-13357 A, JP 57(1982)-161650 A, JP 59(1984)-193354 A, JP 62(1987)-169053 A and JP 3(1991)-30697 A also disclose methods of using complexes of metals such as cobalt, iron, cerium, etc. as oxidizing agents.

DISCLOSURE OF INVENTION

However, in these conventional methods, the accuracy of determination sometimes does not improve sufficiently depending on the samples. Also, as mentioned earlier, since glycated proteins in blood are significant indicators in the diagnosis, therapy and the like of diabetes, it has been desired that the method for measuring them by using a redox reaction achieve a still higher accuracy of determination.

Accordingly, it is an object of the present invention to provide a highly reliable method for measuring an analyte in a sample by using a redox reaction.

In order to achieve the above-mentioned objects, a measuring method according to the present invention is a method for measuring an analyte in a sample containing hemoglobin or a hemoglobin degradation product by using a redox reaction, including adding at least one of a sulfonic acid compound and a nitro compound to the sample so as to eliminate an influence of the hemoglobin or the hemoglobin degradation product contained in the sample.

The inventors of the present invention found that (i) the conventional methods described above merely eliminate the influence of low-molecular-weight reducing substances such as the AsA and GSH but do not eliminate that of high-molecular-weight reducing substances such as proteins and the like and further (ii) the treatment of the sample with a tetrazolium compound eliminates not only the influence of the low-molecular-weight reducing substances but also the influence of the high-molecular-weight reducing substances, especially that of hemoglobin and a hemoglobin degradation product hereinafter, both of them are altogether referred to as "hemoglobin") as a redox substance. With regard to these findings, the applicant filed another application. However, because of its low solubility, it is difficult to make the above-noted tetrazolium compound correspond to hemoglobin contained in samples with a high concentration. Since the tetrazolium compound itself is oxidative, there has been a problem that it may act on the substrate that develops color by oxidation, thus developing erroneous color. In this context, the inventors of the present invention conducted a keen study with a view to eliminating the influence of hemoglobin without affecting the measurement system. As a result, the inventors found that, by treating the sample with a sulfonic acid compound and a nitro compound, the influence of hemoglobin was prevented without affecting the measurement system, thus arriving at the present invention. With such a measuring method of the present invention, it becomes possible to conduct a still more accurate determination, which is useful for various tests in clinical medicine as described above.

BEST MODE FOR CARRYING OUT THE INVENTION

As described above, the measuring method according to the present invention is a method for measuring an analyte in a sample by using a redox reaction, including adding at least one of a sulfonic acid compound and a nitro compound to the sample, thereby eliminating an influence of the hemoglobin contained in the sample on a measurement system.

More specifically, it is preferable that, prior to the redox reaction, at least one of the sulfonic acid compound and the nitro compound is added to the sample so as to eliminate the influence of the hemoglobin or the hemoglobin degradation product contained in the sample and thereafter, the method further includes forming an oxidizing substance or a reducing substance derived from the analyte, measuring the amount of the formed substance derived from the analyte by the redox reaction, and determining the amount of the analyte from the measurement value indicating the amount of the formed substance.

In the present invention, the substance to be added for eliminating the influence of hemoglobin may be either one of the sulfonic acid compound and the nitro compound, for example. However, it is preferable that both of these compounds are added to the sample because the influence can be eliminated even further. When both of the sulfonic acid compound and the nitro compound are added, they need not be added in any particular order and may be added at the same time or at separate times.

In the present invention, the sulfonic acid compound can be a compound represented by, for example, a general formula: $R-SO_3X$.

In the above formula, X is, for example, Na, K, Li, H or the like, and R preferably is a hydrophobic group, for example, $CH_3(CH_2)_n-$, $CH_3(CH_2)-C_6H_4-$, $C_6H_5-$, $C_6H_5-N=N-C_6H_4-$, $C_6H_5-CH=-C_6H_4-$ or the like. For example, n in the above R ranges from 1 to 20. In the above R, "H" may be substituted by an acyl group, a nitro group, a nitroso group, a phenyl group, an alkyl group, and an alkyl ether group or the like.

Specific examples of the sulfonic acid compound include, for example, sodium lauryl sulfate (hereinafter, referred to as "SLS"), dodecylbenzenesulfonic acid sodium salt (hereinafter, referred to as "SDBS"), lithium lauryl sulfate (hereinafter, referred to as "LiLS"), 4-aminoazobenzene-4'-sulfonic acid sodium salt (hereinafter, referred to as "ABSA"), 4-amino-4'-nitrostilbene-2,2'-disulfonic acid disodium salt (hereinafter, referred to as "ANDS"), 4,4'-diazidostilbene-2,2'-disulfonic acid disodium salt (hereinafter, referred to as "DADS"), N-cyclohexyl-2-aminoethane sulfonic acid, N-cyclohexyl-3-aminopropane sulfonic acid, N-cyclohexyl-2-hydroxy-3-aminopropane sulfonic acid, piperazine-1,4-bis(2-ethane sulfonic acid), bathophenanthroline sulfonic acid and the like, and the sulfonic acid compound more preferably is SLS, SDBS or LiLS.

In the present invention, the nitro compound is not particularly limited but can be, for example, a nitrobenzene compound or a dinitrobenzene compound. A benzene ring of these compounds preferably has not only the nitro group but also a substituent such as $-NH_2$, $-OH$, $-COOH$, $-SO_3$ or $-(CH_2)_nCH_3$ (n=2 to 9) and, among them, preferably has a hydrophilic group as the substituent. The substituent can be, for example, a halogen group, an ether group or a phenyl group.

Specific examples of the nitro compound include, for example, 2,4-dinitrophenol (2,4-DNP), 2,5-dinitrophenyl, 2,6-dinitrophenyl, 4,6-dinitro-2-methyl phenol, 2-amino-4-nitrophenol, 2-amino-5-nitrophenol, p-nitrophenol (p-NP), 2,4-dinitroaniline (2,4-DNA), p-nitroaniline (p-NA), sodium nitrite ($NaNO_2$), potassium nitrite ($KNO_2$), 4-amino-4'-nitrostilbene-2,2'-disulfonic acid disodium salt (hereinafter, referred to as "ANPS"), nitrobenzene and the like.

When using both the sulfonic acid compound and the nitro compound, there is no particular limitation on the combination thereof.

Since these sulfonic acid compound and nitro compound have a higher solubility than, for example, the tetrazolium compound mentioned above, they can be treated easily even when the concentration of hemoglobin in the sample is high. Also, in view of their inexpensiveness, the sulfonic acid compound and nitro compound are very useful.

In the measuring method according to the present invention, the amount of the sulfonic acid compound and nitro compound to be added is not particularly limited but can be determined suitably depending on the kind of sample, the amount of hemoglobin contained in the sample, the amount of other reducing substances, etc. Specific examples follow.

In the case of adding either the sulfonic acid compound or the nitro compound, the compound is added preferably in the range of 0.01 to 1000 µmol, more preferably in the range of 0.03 to 200 µmol and particularly preferably in the range of 0.05 to 40 µmol with respect to 1 µl of the sample.

In the case of adding both the sulfonic acid compound and the nitro compound, the sulfonic acid compound is added preferably in the range of 0.005 to 20 µmol and the nitro compound is added preferably in the range of 0.005 to 25 µmol, and the former is added more preferably in the range of 0.02 to 4 µmol and the latter is added more preferably in the range of 0.01 to 5 µmol with respect to 1 µl of the sample.

In the present invention, it is preferable that the redox reaction is a color development reaction caused by reducing the oxidizing substance derived from the analyte and oxidizing a substrate that develops color by oxidation (a chromogenic substrate) using an oxidase, and the amount of the oxidizing substance is measured by measuring a degree of the color developed in the color development reaction. The degree of the color developed is measured by, for example, measuring an absorbance at a wavelength for detecting the substrate.

The chromogenic substrate can be, for example, N-(carboxymethylaminocarbonyl)-4,4'-bis(dimethylamino)diphenylamine sodium salt (hereinafter, referred to as "DA-64"), a combination of Trinder's reagent and 4-aminoantipyrine, N,N,N',N',N'',N''-hexa(3-sulfopropyl)-4,4',4''-triaminotriphenylmethane hexasodium salt (hereinafter, referred to as "TPM-PS"), N,N,N',N',N'',N''-hexa(2-hydroxy-3-sulfopropyl)-4,4',4''-triaminotriphenylmethane hexasodium salt hereinafter, referred to as "TPM-OS"), 10-(carboxymethylaminocarbonyl)3,7-bis(dimethylamino) phenothiazine sodium salt (hereinafter, referred to as "DA-67"), 10-(methylaminocarbonyl)3,7-bis(dimethylamino) phenothiazine (hereinafter, referred to as "MCDP"), 10-(carboxyaminomethyl-4-benzaminocarbonyl)3,7-bis(dimethylamino) phenothiazine sodium salt (hereinafter, referred to as "MMX") or the like. Among the above, triphenylmethane-based chromogenic substrates such as TPM-PS and TPM-OS are preferable, and in particular, triaminotriphenylmethane-based chromogenic substrates are preferable.

The Trinder's reagent can be, for example, phenols, phenol derivatives, aniline derivatives, naphthols, naphthol derivatives, naphthylamine or naphthylamine derivatives. The compound to be combined with the Trinder's reagent may be not only 4-aminoantipyrine noted above but also, for example, aminoantipyrine derivatives, vanillin diamine sulfonic acid, methyl benzothiazolinone hydrazone (MBTH), sulfonated methyl benzothiazolinone hydrazone (SMBTH) or the like.

The chromogenic substrates illustrated above usually have an absorbance at 400 nm or longer. Thus, in the case of using the above-described tetrazolium compound also having an absorbance at 400 nm or longer, the presence of the tetrazolium compound may cause error in the measurement value. On the other hand, the sulfonic acid compound and the nitro compound illustrated above do not have an absorbance at 400 nm or longer, so that there is no need to worry about the error caused in the absorbance measurement even when used with these chromogenic substrates.

Although there is no particular limitation on the combination of these chromogenic substrates with the sulfonic acid compound and the nitro compound, the following combinations are preferable for achieving an accurate color development reaction, for example. Incidentally, the reason that the accuracy of color development reaction improves according to the combination of the chromogenic substrates with the sulfonic acid compound and the nitro compound is not known.

In the case where the chromogenic substrate is DA-64 or a combination of the Trinder's reagent and 4-aminoantipyrine, it is preferable to add both of the sulfonic acid compound and the nitro compound to the sample. For example, the sulfonic acid compound preferably is SLS, SDBS or LiLS, and the nitro compound preferably is 2,4-DNA, 2,4-DNP, PNA or PNP.

On the other hand, in the case where the chromogenic substrate is TPM-PS, TPM-OS, DA-67, MCDP or MMX, it is preferable to add the sulfonic acid compound to the reagent, and it is more preferable to add both of the sulfonic acid compound and the nitro compound to the reagent.

In the present invention, it is preferable that the oxidizing substance derived from the analyte is hydrogen peroxide. It is also preferable that the oxidase is a peroxidase.

In the measuring method of the present invention, the kind of the sample is not particularly limited. Other than blood samples such as whole blood, plasma, serum and blood cells, the samples can be, for example, biological samples such as urine, spinal fluid and saliva, drinks such as juices, or foods such as soy sauce and Worcestershire sauce.

In the measuring method of the present invention, the analyte is not particularly limited as long as it utilizes a redox reaction but may be, for example, components in whole blood, components in erythrocytes, components in plasma, components in serum and the like, and it preferably is a component in erythrocytes. More specifically, the analyte may be, for example, glycated proteins such as glycated hemoglobin and glycated albumin, glycated peptides, glycated amino acids, glucose, uric acid, cholesterol, creatinine, sarcosine, glycerol and the like. Among these, glycated proteins are more preferable. For example, when a component in erythrocytes is to be measured, whole blood itself may be hemolyzed to prepare a sample, or erythrocytes are separated from whole blood and hemolyzed to prepare a sample.

In the measuring method of the present invention, when the analyte is a glycated protein, it is preferable that a FAOD is caused to act on the glycated protein so that hydrogen peroxide is formed as the oxidizing substance derived from the analyte. The glycated portion of the glycated protein is oxidized and decomposed by the FAOD, thereby generating the hydrogen peroxide. Also, when the analyte is a glycated amine such as a glycated peptide or a glycated amino acid, it is preferable that the analyte similarly is subjected to the action of a FAOD. Moreover, it is preferable that glycated proteins and glycated peptides are treated with a protease before the FAOD treatment as necessary.

As the FAOD, a FAOD catalyzing a reaction represented by Formula (1) below preferably is used.

$$R^1-CO-CH_2-NH-R^2+H_2O+O_2 \rightarrow R^1-CO-CHO+NH_2-R^2+H_2O_2 \quad (1)$$

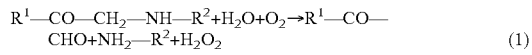

In Formula (1), $R^1$ represents a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by $$-[CH(OH)]_n-CH_2OH$$

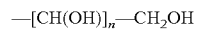

where n is an integer of 0 to 6.

In Formula (1), $R^2$ is not particularly limited. However, when the substrate is a glycated amino acid, a glycated peptide or a glycated protein, for example, there is a difference between the case where an α-amino group is glycated and the case where an amino group other than the α-amino group is glycated.

In Formula (1), when an α-amino group is glycated, $R^2$ is an amino acid residue or a peptide residue represented by Formula (2) below.

$$-CHR^3-CO-R^4 \quad (2)$$

In Formula (2), $R^3$ denotes an amino-acid side chain group. $R^4$ denotes a hydroxyl group, an amino acid residue or a peptide residue, and can be represented, for example, by Formula (3) below. In Formula (3), n is an integer of 0 or larger, and $R^3$ denotes an amino-acid side chain group as in the above.

$$-(NH-CHR^3-CO)_n-OH \quad (3)$$

In Formula (1) above, when an amino group other than the α-amino group is glycated (i.e., an amino-acid side chain group is glycated), $R^2$ can be represented by Formula (4) below.

$$-R^5-CH(NH-R^6)-CO-R^7 \quad (4)$$

In Formula (4) above, $R^5$ denotes a portion other than the glycated amino group in the amino-acid side chain group. For example, when the glycated amino acid is lysine, $R^5$ is as follows.

$$-CH_2-CH_2-CH_2-CH_2-$$

For another example, when the glycated amino acid is arginine, $R^5$ is as follows.

$$-CH_2-CH_2-CH_2-NH-CH(NH_2)-$$

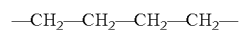

In Formula (4) above, $R^6$ denotes hydrogen, an amino acid residue or a peptide residue, and can be represented, for example, by Formula (5) below. In Formula (5), n denotes an integer of 0 or lager, and $R^3$ denotes an amino-acid side chain group as in the above.

$$-(CO-CHR^3-NH)_n-H \quad (5)$$

In Formula (4) above, $R^7$ denotes a hydroxyl group, an amino acid residue or a peptide residue, and can be represented, for example, by Formula (6) below. In Formula (6), n is an integer of 0 or lager, and $R^3$ denotes an amino-acid side chain group as in the above.

$$-(NH-CHR^3-CO)_n-OH \quad (6)$$

First Embodiment

In the following, the measuring method of the present invention will be described with reference to the examples in which a glycated protein in blood cells is measured.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited and can be, for example, a method using a surfactant, a method using ultrasonic waves, a method utilizing a difference in osmotic pressure or the like. Among these, the method using a surfactant is preferable because of its simplicity in operation, etc.

As the surfactant, for example, nonionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants) and the like can be used. Specific examples thereof are Triton X-100, Tween-20, Brij 35, etc. The conditions of the treatment with the surfactant usually are as follows: when the concentration of blood cells in the solution to be treated is 1 to 10 vol %, the surfactant is added so that its concentration in the solution falls in the range from 0.01 to 5 wt %, and stirred at room temperature for about several seconds (about 5 seconds) to 10 minutes.

Next, at least one of a sulfonic acid compound and a nitro compound is added to the hemolyzed sample to carry out pretreatment of the hemolyzed sample.

Although either one of or both of the sulfonic acid compound and the nitro compound may be added, it is preferable to make decisions suitably according to the kinds of chromogenic substrates to be used in a later step as described above.

In the case of adding either one of the sulfonic acid compound and the nitro compound, the amount to be added is not particularly limited but can be in the above-described addition ratio. More specifically, when the concentration of blood cells in the solution to be pretreated is 1 vol %, the concentration of the nitro compound ranges, for example, from 0.05 to 500 mmol/L and preferably from 0.2 to 100 mmol/L. Also, when the concentration of blood cells in the solution to be pretreated is 1 vol %, the concentration of the sulfonic acid compound ranges, for example, from 0.05 to 200 mmol/L and preferably from 0.2 to 40 mmol/L.

Also, in the case of adding both of the sulfonic acid compound and the nitro compound to the sample, the amount to be added is not particularly limited but can be in the above-described addition ratio. More specifically, when the concentration of blood cells in the solution to be pretreated is 1 vol %, the concentration of the sulfonic acid compound ranges, for example, from 0.05 to 200 mmol/L and that of the nitro compound ranges, for example, from 0.05 to 250 mmol/L, and the former ranges preferably from 0.2 to 40 mmol/L and the latter ranges preferably from 0.1 to 50 mmol/L. When both of the sulfonic acid compound and the nitro compound are added, they need not be added in any particular order as described above and may be added at the same time.

Although the sulfonic acid compound and the nitro compound may be used as they are, they preferably are dissolved in solvents and used as a sulfonic acid compound solution and a nitro compound solution in view of simplicity of operation and treatment efficiency. The concentration of each of these solutions can be determined suitably depending on the kinds or the like. The concentration of the sulfonic acid compound solution ranges, for example, from 5 to 1000 mmol/L and ranges preferably from 5 to 400 mmol/L, and that of the nitro compound solution ranges, for example, from 0.5 to 100 mmol/L and preferably from 1 to 50 mmol/L. As the solvent, it is possible to use distilled water, a physiological salt solution, buffers and the like, and the buffer can be those listed below. Incidentally, both of the above compounds may be an individual or a combination of two or more.

This pretreatment usually is carried out in a buffer. Examples of the buffer include amine buffers, phosphate buffers, borate buffers and Good's buffers such as MOPS buffer, CHES buffer, CAPS buffer, CAPSO buffer and the like. Examples of buffer agents contained in the amine buffers include glycine, ethylamine, diethylamine, methylamine, dimethylamine, trimethylamine, Tris(hydroxymethyl)aminomethane, triethanolamine, glycinamide, and the like.

The pH of the above buffers preferably ranges from 7 to 12, more preferably from 8 to 11, and particularly preferably from 8 to 10.

The conditions of this pretreatment are not specifically limited. However, the pretreatment usually is carried out at a temperature ranging from 10° C. to 37° C. and for a period of 10 seconds to 60 minutes.

In the case of using the above-described sodium lauryl sulfate or the like as the sulfonic acid compound to be used for this pretreatment, it is possible to carry out the above-described hemolysis and this pretreatment at the same time by adding a single substance (i.e., sodium lauryl sulfate or the like) since sodium lauryl sulfate itself functions as the surfactant.

Next, the pretreated hemolyzed sample is treated with a protease. This treatment is performed so that the FAOD used in the subsequent treatment may act on the analyte more easily.

The kind of the protease is not particularly limited, and for example, protease K, subtilisin, trypsin, aminopeptidase, metalloprotease and the like can be used. The conditions of the protease treatment are determined suitably depending on the kind of the protease used, the kind and concentration of the glycated protein as the analyte, etc.

More specifically, when the pretreated hemolyzed sample is treated using protease K as the protease, usually, the concentration of the protease in the reaction solution ranges from 10 to 30,000 mg/L, the concentration of blood cells in the reaction solution ranges from 0.05 to 15 vol %, a reaction temperature ranges from 15° C. to 37° C., a reaction period ranges from 1 minute to 24 hours, and a pH ranges from 6 to 12. This protease treatment usually is carried out in a buffer. As the buffer, it is possible to use a buffer similar to that in the pretreatment.

Next, a degradation product obtained by the protease treatment further is treated with the FAOD. This FAOD treatment catalyzes the reaction shown by Formula (1) above.

It is preferable that the FAOD treatment is carried out in a buffer as in the above protease treatment. The conditions of the FAOD treatment are determined suitably depending on the kind of the FAOD used, the kind and concentration of the glycated protein as the analyte, etc.

More specifically, the conditions are as follows: the concentration of the FAOD in the reaction solution ranges from 50 to 50,000 U/L, the concentration of blood cells in the reaction solution ranges from 0.01 to 1 vol %, a reaction temperature ranges from 15° C. to 37° C., a reaction period ranges from 1 to 60 minutes, and a pH ranges from 6 to 9. Moreover, the kind of the buffer is not particularly limited, and for example, the buffers similar to those in the protease treatment can be used.

Next, the hydrogen peroxide formed in the FAOD treatment is measured by a redox reaction using a POD and the chromogenic substrate.

The redox reaction usually is carried out in a buffer. The conditions of the reaction are determined suitably depending on the concentration of the hydrogen peroxide formed, etc.

The conditions are usually as follows: the concentration of the POD in the reaction solution ranges from 10 to 100,000 IU/L, the concentration of the chromogenic substrate ranges from 0.005 to 30 mmol/l, a reaction temperature ranges from 15° C. to 37° C., a reaction period ranges from 0.1 to 30 minutes, and a pH ranges from 5 to 9. Moreover, the kind of the buffer is not particularly limited, and for example, the buffers similar to those in the protease treatment and the FAOD treatment can be used.

In the redox reaction, for example, when the chromogenic substrate is used, the amount of the hydrogen peroxide can be determined by measuring the degree of the color developed (i.e. absorbance) in the reaction solution with a spectrophotometer. Then, using this concentration of the hydrogen peroxide and a calibration curve or the like, for example, the amount of the glycated protein in the sample can be determined.

The amount of the hydrogen peroxide can be determined not only by the abovedescribed enzymatic method using a POD or the like but also by an electrical method, for example.

In this method for measurement, the pretreatment step with the sulfonic acid compound and the nitro compound is not particularly limited as long as it is carried out before the redox reaction actually occurs as described above. However, because the hydrogen peroxide is formed after the FAOD treatment, it is preferable that the pretreatment step is performed before the FAOD treatment. Moreover, although each of the treating steps may be carried out separately as described above, some of the treating steps also may be performed simultaneously, for example, in the combinations as follows:

1: hemolysis treatment+pretreatment
2: hemolysis treatment+pretreatment+protease treatment
3: protease treatment+FAOD treatment
4: FAOD treatment+POD redox treatment
5: protease treatment+FAOD treatment+POD redox treatment Furthermore, the order of adding the sulfonic acid compound and the nitro compound and the order of adding the FAOD, the POD and the chromogenic substrate also are not particularly limited.

With this method, by contacting the sample with the sulfonic acid compound and the nitro compound, it is possible to eliminate not only the influence of low-molecular-weight reducing substances such as GSH, AsA, dithiothreitol, cysteine and N-acetyl-cysteine, but also the influence of hemoglobin and hemoglobin degradation products, in particular, as reducing substances. Consequently, a highly accurate determination can be performed without affecting the redox reaction and the absorbance measurement, for example.

Furthermore, in the pretreatment step in the measuring method of the present invention, for example, oxidizing agents and enzymes other than the sulfonic acid compound and the nitro compound further may be used in combination. Examples of the oxidizing agents include EDTA-Fe and halogen oxides such as sodium iodoacetate, iodic acid and periodic acid, and examples of the enzymes include ascorbic acid oxidase and bilirubin oxidase. The amount of such an oxidizing agent to be added ranges, for example, from 0.001 to 0.1 mg with respect to 1 µl of the sample.

In the measuring method of the present invention, the analyte is not particularly limited as long as a redox reaction is utilized. Examples of the analyte other than the glycated protein include glycated peptides, glycated amino acids, glucose, cholesterol, uric acid, creatinine, sarcosine and glycerol, as described above.

When the amount of each of the above-described examples of the analyte is measured by forming hydrogen peroxide, it is appropriate to form the hydrogen peroxide, for example, by action of: a glucose oxidase on the glucose; a cholesterol oxidase on the cholesterol; a uricase on the uric acid; a sarcosine oxidase on the creatinine; a sarcosine oxidase on the sarcosine; or a glycerol oxidase on the glycerol; respectively. The amount of the hydrogen peroxide can be measured in the manner similar to that described above. Moreover, glycated peptides and glycated amino acids can be measured, for example, in the manner similar to the measurement of the glycated protein described above.

Furthermore, after the treatment of hemoglobin and hemoglobin degradation products in a sample with the sulfonic acid compound and the nitro compound, in the case of forming a reducing substance derived from the analyte, measuring the amount of the reducing substance by a redox reaction and then determining the amount of the analyte from the measurement value, the measurement can be carried out, for example, in the following manner.

When the analyte is glucose, for example, a reducing substance such as NADH or NADPH is formed using glucose dehydrogenase in the presence of $NAD^+$, $NADP^+$ or the like. Then, the NADH or NADPH as a reducing substance derived from the analyte is measured by a redox reaction, using, for example, diaphorase and a substrate that develops color by reduction. Then, as described above, the amount of the analyte in the sample can be determined using the concentration of the reducing substance derived from the analyte and a calibration curve or the like. Furthermore, for example, cholesterol dehydrogenase can be used when the analyte is cholesterol, and sarcosine dehydrogenase can be used when the analyte is sarcosine.

As the substrate that develops color by reduction, although not particularly limited, for example, the abovementioned chromogenic tetrazolium compound, 2,6-dichlorophenolindophenol or the like can be used.

EXAMPLES

Hereinafter, examples will be described together with comparative examples.

Example 1

In Example 1, using TPM-PS as a chromogenic substrate, a hemoglobin sample containing fructosyl valine (in the following, referred to as "FV") was treated with a sulfonic acid compound and a nitro compound, thus measuring the amount of FV. The sample and reagents used here and the method will be described below.

(Preparation of Sample to be Measured)

Lyophilized hemoglobin was dissolved in purified water, thus preparing a 50 g/L hemoglobin solution. On the other hand, FV was produced and dissolved in purified water, thus preparing a 1 mM FV solution. Then, 37 µl of the hemoglobin solution, 60 µl of the FV solution and 203 µl of purified water were mixed so as to prepare a sample to be measured.

(First reagent)

| | |
|---|---|
| Sulfonic acid compound | 3.2 mM, 6.4 mM or 12.8 mM |
| Surfactant (polyoxyethylene(9)dodecyl ether) | 1.85 g/L |
| CHES—CHES · Na buffer (pH 9.4) | 40 mM |
| MOPS—MOPS · Na buffer (pH 9.4) | 15 mM |

As the sulfonic acid compound of the first reagent, SLS (manufactured by Nacalai Tesque, Inc.), SDBS (manufactured by Wako Pure Chemical Industries, Ltd.), ABSA (manufactured by Tokyo Kasei Kogyo Co., Ltd.), ANDS (manufactured by Tokyo Kasei Kogyo Co., Ltd.) and DADS (manufactured by Tokyo Kasei Kogyo Co., Ltd.) were used individually.

(Second reagent)

| | |
|---|---|
| Nitro compound (2,4-DNA; manufactured by Wako Pure Chemical Industries, Ltd.) | 0 mM or 6.4 mM |
| Metalloprotease (manufactured by ARKRAY, INC.) | 2.0 MU/L |
| $CaCl_2$ | 2.5 mM |
| NaCl | 50 mM |
| MOPS—MOPS · Na buffer (pH 6.5) | 1.0 mM |

(Third reagent)

| | |
|---|---|
| FAOD (manufactured by ARKRAY, INC.) | 18 KU/L |
| POD (manufactured by Kikkoman Corporation) | 67 KU/L |
| $CaCl_2$ | 2.5 mM |
| TPM-PS (manufactured by DOJINDO LABORATORIES) | 0.25 mM |
| ADA buffer (pH 7.0) | 300 mM |

(Method)

After 8.26 µL of the first reagent was added to 0.14 µL of the sample to be measured, 75.6 µL of the second reagent further was mixed therein and allowed to stand at 37° C. for 5 minutes. Then, 18.9 µL of the third reagent was blended into this mixture and incubated at 37° C. so as to allow a color development reaction. The absorbance after 5 minutes was measured with trade name JCA-BM8 (manufactured by JEOL. Ltd.). The measurement wavelengths were set to 571 nm for the main wavelength and 805 nm for the sub-wavelength. On the other hand, in the Comparative Example, the absorbance was measured similarly to Example 1 described above except that the sulfonic acid compound in the first reagent and the nitro compound in the second reagent were not added. When the first reagent and the second reagent were mixed into the samples, the amounts of the added sulfonic acid compound were 0.189 µmol, 0.378 µmol and 0.755 µmol and the amount of the added nitro compound was 3.46 µmol with respect to 1 µL of the sample.

TABLE 1

| | | Sulfonic acid compound (mM) | Nitro compound (mM) | Absorbance (mAbs) |
|---|---|---|---|---|
| Example | 1-1 | SLS (3.2) | 2,4-DNA (0.9) | 149 |
| | 1-2 | SLS (6.4) | 2,4-DNA (0.9) | 154 |
| | 1-3 | SLS (12.8) | 2,4-DNA (0.9) | 160 |

TABLE 1-continued

| | | Sulfonic acid compound (mM) | Nitro compound (mM) | Absorbance (mAbs) |
|---|---|---|---|---|
| | 1-4 | SDBS (6.4) | 2,4-DNA (0.9) | 121 |
| | 1-5 | SLS (6.4) | — | 154 |
| | 1-6 | ABSA (6.4) | — | 132 |
| | 1-7 | ANDS (6.4) | — | 113 |
| | 1-8 | DADS (6.4) | — | 124 |
| Comparative Example 1 | | — | — | 30 |

As shown in Table 1, in Example 1, with each of the sulfonic acid compounds or the combination thereof with the nitro compound, the absorbance indicating the FV amount in the samples increased compared with the Comparative Example. These results show that, according to Example 1, the sulfonic acid compound and the nitro compound eliminated the influence of hemoglobin in the samples.

Example 2

In Example 2, using DA-64 as a chromogenic substrate, a hemoglobin sample containing FV was treated with a sulfonic acid compound and a nitro compound, thus measuring the amount of FV The sample and reagents used here and the method will be described below.

(Preparation of Sample to be Measured)

60 µl of the hemoglobin solution prepared in Example 1 above, 37 µl of the FV solution and 203 µl of purified water were mixed so as to prepare a sample to be measured.

(First reagent)

| | |
|---|---|
| Sulfonic acid compound (SLS: manufactured by Nacalai Tesque, Inc.) | 6.4 mM |
| Surfactant (polyoxyethylene(9)lauryl ether) | 1.85 g/L |
| CHES—CHES · Na buffer (pH 9.4) | 40 mM |
| MOPS—MOPS · Na buffer (pH 9.4) | 15 mM |

(Second reagent)

| | |
|---|---|
| Nitro compound | 0.9 mM |
| Metalloprotease (manufactured by ARKRAY, INC.) | 2.0 MU/L |
| $CaCl_2$ | 2.5 mM |
| NaCl | 50 mM |
| MOPS—MOPS · Na buffer (pH 6.5) | 1.0 mM |

As the nitro compound, 2,4-DNA (manufactured by Wako Pure Chemical Industries, Ltd.), p-NA (manufactured by Wako Pure Chemical Industries, Ltd.), p-NP (manufactured by Wako Pure Chemical Industries, Ltd.), $NaNO_2$ (manufactured by Nacalai Tesque, Inc.), and 2,4-DNH (manufactured by Wako Pure Chemical Industries, Ltd.) were used individually. In the case of adding two kinds of the nitro compound, a total of 1.8 mM (0.9 mM each) was added.

(Third reagent)

| | |
|---|---|
| FAOD (manufactured by ARKRAY, INC.) | 17.5 KU/L |
| POD (manufactured by Kikkoman Corporation) | 67 KU/L |

-continued

| (Third reagent) | |
|---|---|
| DA-64 (manufactured by Wako Pure Chemical Industries, Ltd.) | 70 μM |
| Tris-HCL buffer (pH 7.0) | 300 mM |

(Method)

After 8.26 μL of the first reagent was added to 0.14 μL of the sample to be measured, 75.6 μL of the second reagent further was mixed therein and allowed to stand at 37° C. for 5 minutes. Then, 18.9 μL of the third reagent was blended into this mixture and incubated at 37° C. so as to allow a color development reaction. The absorbance after 5 minutes was measured with trade name JCA-BM8 (manufactured by JEOL. Ltd.). The measurement wavelengths were set to 751 nm for the main wavelength and 805 nm for the sub-wavelength. On the other hand, in the Comparative Example, the absorbance was measured similarly to Example 2 described above except that the sulfonic acid compound in the first reagent and the nitro compound in the second reagent were not added. The results are shown in Table 2 below.

TABLE 2

| | | Sulfonic acid compound (mM) | Nitro compound (mM) | Absorbance (mAbs) |
|---|---|---|---|---|
| Example | 2-1 | SLS (6.4) | 2,4-DNA (0.9) | 51.3 |
| | 2-2 | SLS (6.4) | p-NA (0.9) | 41.0 |
| | 2-3 | SLS (6.4) | p-NP (0.9) | 41.5 |
| | 2-4 | SLS (6.4) | $NaNO_2$ (0.9) | 41.5 |
| | 2-5 | SLS (6.4) | 2,4-DNA (0.9) p-NP (0.9) | 277.0 |
| | 2-6 | SLS (6.4) | 2,4-DNA (0.9) p-NA (0.9) | 279.0 |
| | 2-7 | SLS (6.4) | p-NP (0.9) p-NA (0.9) | 267.0 |
| | 2-8 | SLS (6.4) | 2,4-DNA (0.9) $NaN_3$ (0.9) | 257.0 |
| Comparative Example 2 | | — | — | 2.1 |

As shown in Table 2, in Example 2, with the combination of the sulfonic acid compound and the nitro compounds, the absorbance indicating the FV amount in the samples increased compared with the Comparative Example. Furthermore, by adding twice as much nitro compound, the absorbance increased even further. These results show that, according to Example 2, the sulfonic acid compound and the nitro compound eliminated the influence of hemoglobin in the samples.

INDUSTRIAL APPLICABILITY

As described above, in the measuring method according to the present invention, by adding the sulfonic acid compound and the nitro compound to the samples, it is possible to eliminate the influence of hemoglobin in the samples as the reducing substance, thus allowing a highly-reliable measurement. Accordingly, the measuring method of the present invention can be applied to various analyses in clinical medicine, for example, and are particularly useful for measuring glycated proteins, such as glycated hemoglobin in erythrocytes, that are significant in diagnosis of diabetes.

The invention claimed is:

1. A method for measuring an analyte in a sample containing hemoglobin by using a redox reaction, comprising:
    prior to the redox reaction, adding at least one of a sulfur-containing compound selected from the group consisting of dodecylbenzenesulfonic acid sodium salt, 4-aminoazobenzene-4'-sulfonic acid sodium salt, 4-amino-4'-nitrostilbene-2-2'-disulfonic acid disodium salt, and 4,4'-diazidostilbene-2,2'-disulfonic acid disodium salt, or adding a combination of at least one of said sulfur-containing compounds and at least one of a nitrogen-containing compound selected from the group consisting of 2,4-dinitrophenol, p-nitrophenol, 2,4-dinitroaniline, p-nitroaniline, 4-amino-4'-nitrostilbene-2,2'-disulfonic acid disodium salt, nitrobenzene, sodium nitrite, and potassium nitrite to the sample so as to eliminate an influence of the hemoglobin contained in the sample and thereafter, the method further comprising:
    forming an oxidizing substance or a reducing substance derived from the analyte by adding an oxidative enzyme;
    measuring the amount of the formed substance derived from the analyte by the redox reaction; and
    determining the amount of the analyte from the measurement value indicating the amount of the formed substance.

2. The method according to claim 1, wherein both of the sulfur-containing compound and the nitrogen-containing compound are added to the sample.

3. The method according to claim 1, wherein the oxidizing substance derived from the analyte is hydrogen peroxide.

4. The method according to claim 1, wherein the redox reaction is a color development reaction using an oxidase, and involves reducing the oxidizing substance derived from the analyte and oxidizing a substrate that develops color by oxidation, and the amount of the oxidizing substance is measured by measuring a degree of the color developed in the color development reaction.

5. The method according to claim 4, wherein the degree of the color developed is measured by measuring an absorbance at a wavelength far detecting the substrate.

6. The method according to claim 4, wherein the oxidase is a peroxidase.

7. The method according to claim 4, wherein the substrate that develops color by oxidation is at least one compound selected from the group consisting of N-(carboxymethylaminocarbonyl)-4,4'-bis(dimethylamino)diphenylamine sodium salt, a combination of Trinder's reagent and 4-aminoantipyrine, N,N,N',N',N'',N''-hexa(2-hydroxy-3-sulfopropyl)-4,4',4''-triaminotriphenylmethane hexasodium salt, 10-(carboxymethylaminocarbonyl)3,7bis(dimethylamino) phenothiazine sodium salt, 10-(methylaminocarbonyl)3,7-bis(dimethylamino) phenothiazine and 10-(carboxyaminomethyl-4-benzaminocarbonyl)3,7-bis(dimethylamino) phenothiazine sodium salt, and both of the sulfur-containing compound and the nitrogen-containing compound are added to the sample.

8. The method according to claim 4, wherein the substrate that develops color by oxidation is at least one compound selected from the group consisting of N,N,N',N',N'',N''-hexa(3-sulfopropyl)-4,4',4''-triaminotriphenylmethane hexasodium salt, N,N,N',N',N'',N''-hexa(2-hydroxy-3-sulfopropyl)-4,4',4''-triaminotriphenylmethane hexasodium salt, 10-(carboxymethylaminocarbonyl)3,7-bis(dimethylamino) phenothiazine sodium salt, 10-(methylaminocarbonyl)3,7-bis(dimethylamino) phenothiazine and 10-(carboxyaminomethyl-4-benzaminocarbonyl)3,7-bis(dimethylamino) phenothiazine sodium salt, and at least the-sulfur-containing compound is added to the sample.

9. The method according to claim 1, wherein the analytic is at least one selected from the group consisting of a glycated protein, a glycated peptide, and a glycated amino acid, and hydrogen peroxide is formed as the oxidizing substance derived from the analyte by allowing a fructosyl amino acid oxidase to act on the analyte in the sample after eliminating influence of the hemoglobin contained in the sample.

10. The method according to claim 9, wherein at least one of the sulfur-containing compound and the nitrogen-containing compound is added to the sample before allowing the fructosyl amino acid oxidase to act on the analyte.

11. The method according to claim 1, wherein the analyte is at least one selected from the group consisting of a glycated protein, a glycated peptide and a glycated amino acid.

12. The method according to claim 11, wherein the glycated protein is glycated hemoglobin.

13. The method according to claim 1, wherein the sample is a hemolyzed sample obtained by hemolyzing erythrocytes.

14. The method according to claim 13, wherein when the sulfur-containing compound is added to the sample, its concentration is 0.05 to 200 mmol/L when a concentration of blood cells in the sample is 1 vol %.

15. The method according to claim 13, wherein when the nitrogen-containing compound is added to the sample, its concentration is (3.05 to 500 mmol/L when a concentration of blood cells in the sample is 1 vol %.

16. The method according to claim 13, wherein when the sulfur-containing compound and the nitrogen-containing compound are added to the sample, their concentrations are 0.05 to 200 mmol/L and 0.05 to 250 mmol/L, respectively, when a concentration of blood cells in the sample is 1 vol %.

17. A method for measuring an analyte in a sample containing hemoglobin by using a redox reaction, comprising:
  prior to the redox reaction, adding at least one of sodium lauryl sulfate and lithium lauryl sulfate to the sample so as to eliminate an influence of the hemoglobin contained in the sample without adding a nitro compound or nitrite salt and thereafter, the method further comprising:
  forming an oxidizing substance or a reducing substance derived from the analyte by adding an oxidative enzyme;
  measuring the amount of the formed substance derived from the analyte by the redox reaction; and
  determining the amount of the analyte from the measurement value indicating the amount of the formed substance.

* * * * *